United States Patent [19]

Daemer

[11] Patent Number: 5,267,861
[45] Date of Patent: Dec. 7, 1993

[54] DENTAL INSTRUMENT COVER

[76] Inventor: Mary E. Daemer, 3232 Glenview St., Philadelphia, Pa. 19149

[21] Appl. No.: 950,145

[22] Filed: Sep. 24, 1992

[51] Int. Cl.⁵ .................................................. A61C 1/16
[52] U.S. Cl. ................................................... 433/116
[58] Field of Search .......................... 433/116, 77, 48; 206/368, 363, 349, 63.5

[56] References Cited

U.S. PATENT DOCUMENTS

| | | | |
|---|---|---|---|
| 2,822,848 | 2/1958 | Thoms | 206/349 X |
| 4,446,967 | 5/1984 | Halkyard | 206/368 |
| 4,660,610 | 4/1987 | McIntire, III | 150/52 R |
| 4,899,877 | 2/1990 | Kiernan | 206/349 |
| 4,930,660 | 6/1990 | Porteous | 220/367 |
| 5,024,326 | 6/1991 | Sandel et al. | 206/366 |

FOREIGN PATENT DOCUMENTS 844565  7/1939  France ................. 206/368

*Primary Examiner*—Gene Mancene
*Assistant Examiner*—Cindy A. Chirichetti
*Attorney, Agent, or Firm*—Leon Gilden

[57] ABSTRACT

A cover structure is arranged to afford protection to a dental instrument utilizing a plurality of hingedly cooperative mirror image cover members formed of a deformable memory retentent material, having polymeric foam therewithin to secure and position a dental instrument member. The invention is arranged to permit orientation of the cover during use of the dental instrument.

5 Claims, 4 Drawing Sheets

DENTAL INSTRUMENT COVER

BACKGROUND OF THE INVENTION

1. Field of the Invention

The field of invention relates to cover structure, and more particularly pertains to a new and improved dental instrument cover wherein the same is uniquely configured to afford protection to a dental instrument minimizing transition of disease and maintaining sanitizing of an associated dental instrument contained within the cover structure.

2. Description of the Prior Art

Individuals utilizing dental instruments such as technicians, dentists, and the like are subject to disease transmission as well as injury due to the pointed and puncturing nature of such dental instrument members. The instant invention attempts to address deficiencies in the prior art by affording protection to an individual during transport and storage of such dental instruments, while permitting positioning of the cover structure during use of the dental instrument and in this respect, the present invention substantially fulfills this need.

SUMMARY OF THE INVENTION

In view of the foregoing disadvantages inherent in the known types of cover structure now present in the prior art, the present invention provides a central instrument cover wherein the same is arranged to afford protection in covering of a dental instrument member. As such, the general purpose of the present invention, which will be described subsequently in greater detail, is to provide a new and improved dental instrument cover which has all the advantages of the prior art cover structure and none of the disadvantages.

To attain this, the present invention provides a cover structure arranged to afford protection to a dental instrument utilizing a plurality of hingedly cooperative mirror image cover members formed of a deformable memory retentent material, having a polymeric foam therewithin to secure and position a dental instrument member. The invention is arranged to permit orientation of the cover during use of the dental instrument.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental instrument cover which has all the advantages of the prior art cover apparatus and none of the disadvantages.

It is another object of the present invention to provide a new and improved dental instrument cover which may be easily and efficiently manufactured and marketed.

It is a further object of the present invention to provide a new and improved dental instrument cover which is of a durable and reliable construction.

An even further object of the present invention is to provide a new and improved dental instrument cover which is susceptible of a low cost of manufacture with regard to both materials and labor, and which accordingly is then susceptible of low prices of sale to the consuming public, thereby making such dental instrument covers economically available to the buying public.

Still yet another object of the present invention is to provide a new and improved dental instrument cover which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
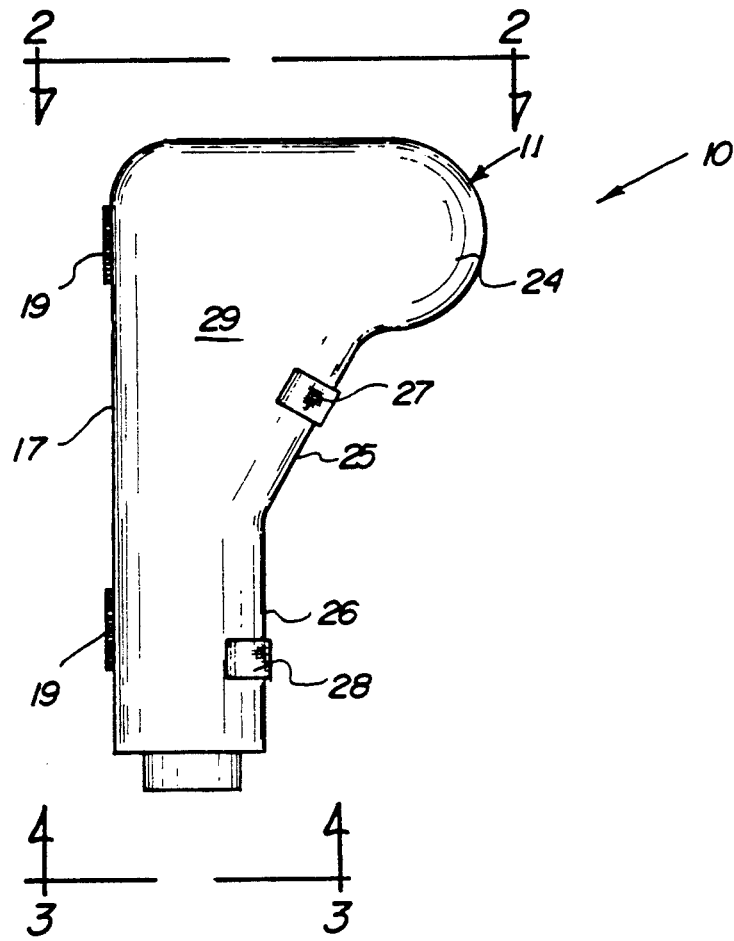
FIG. 1 is an orthographic top view of the instant invention.
Figure 2:
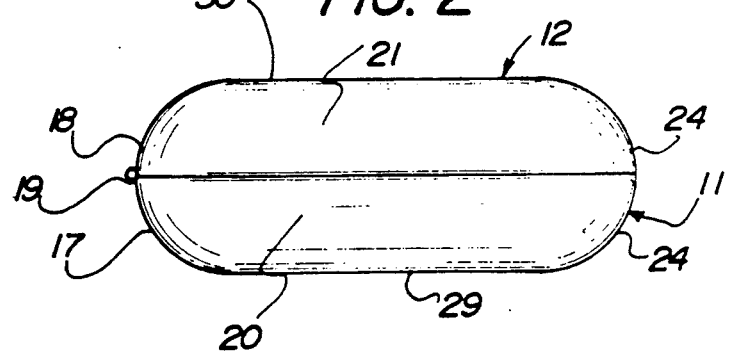
FIG. 2 is an orthographic view, taken along the lines 2—2 of FIG. 1 in the direction indicated by the arrows.
Figure 3:
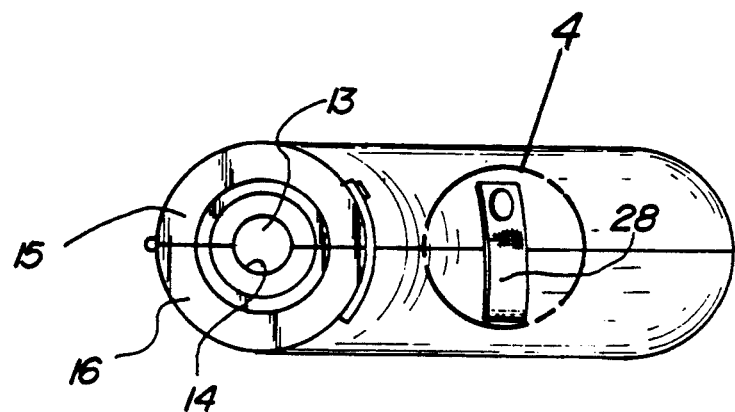
FIG. 3 is an orthographic view, taken along the lines 3—3 of FIG. 1 in the direction indicated by the arrows.
Figure 4:
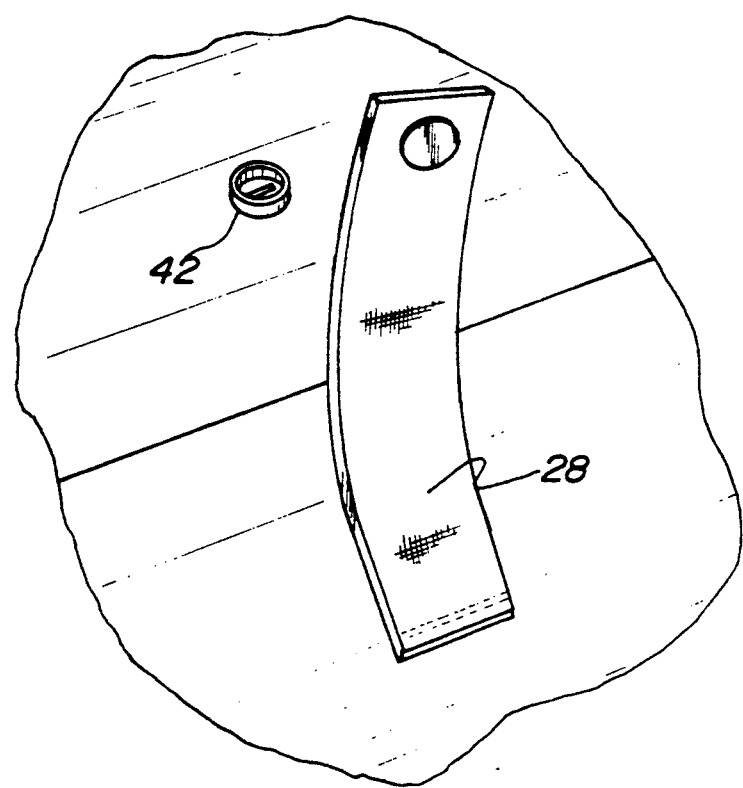
FIG. 4 is an isometric illustration of section 4 as set forth in FIG. 3.
Figure 5:
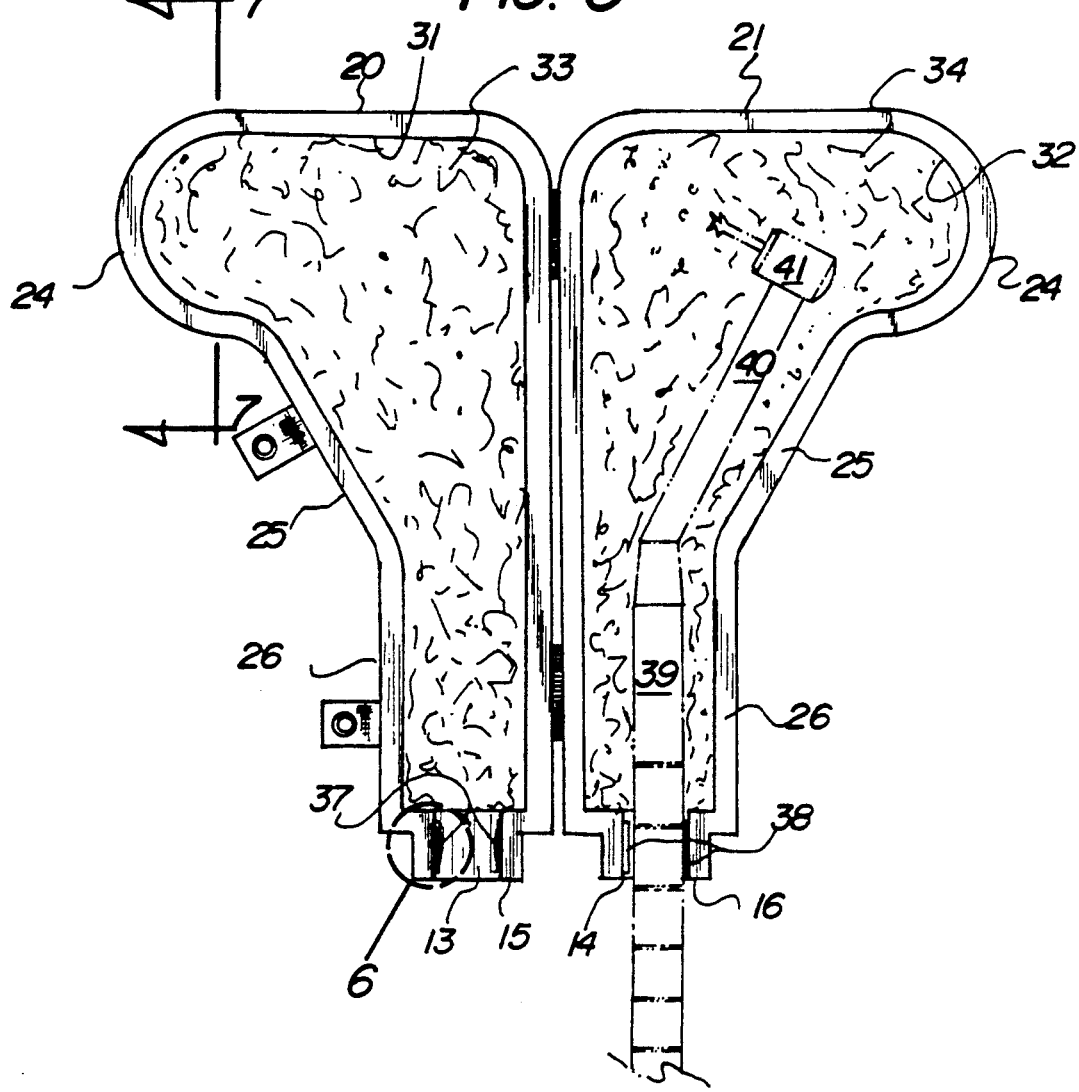
FIG. 5 is an orthographic view of the dental instrument cover structure in an opened configuration indicating mounting of an associated dental instrument member therewithin.

With reference now to the drawings, and in particular to FIGS. 1 to 8 thereof, a new and improved dental instrument cover embodying the principles and concepts of the present invention and generally designated by the reference numeral 10 will be described.

More specifically, the dental instrument cover 10 of the instant invention essentially comprises a first cover 11 coextensive with and in a mirror image relationship relative to a second cover 12. The first cover 11 includes a first cover semi-cylindrical entrance opening 13 through a first cover first end wall 15 that is in turn cooperative with a second cover semi-cylindrical entrance opening 14 directed through a second cover first end wall 16, with the first and second cover first end walls in a coplanar relationship and the first and second cover openings 13 and 14 defining a cylindrical entrance opening in a first position, as illustrated in FIG. 1. The cover structure is openable to a second position about hinge members 19 (see FIG. 5), as the hinge members 19 are in turn mounted to first and second cover linear first side walls 17 and 18. A first cover second end wall and a second cover second end wall 20 and 21 are of a second end wall length greater than a first end wall width of the first and second cover first end walls 15 and 16 to accommodate a head portion 41 positioned within the cover 10 in adjacency to the first and second cover second end walls 20 and 21. The first cover and the second cover include each a second side wall spaced from the respective second side walls, with the second side walls of an angulated configuration, as indicated in FIG. 1. Each of the second side walls includes a second side wall first portion 24 having a first portion spacing relative to the first end cover first side wall 17 and 18 that is greater than the second end wall length to more readily accommodate various instruments of angulated configuration and their head portions 41 as indicated. The second side walls each include a third side wall portion extending from the first and second covers first end walls 15 and 16, and oriented in a generally parallel relationship relative to the first cover first side walls 17 and 18. A second side wall second portion 25 intermediate the first and third portion are arranged in a canted relationship relative to the first portions 24 to the third portions 26. Dental instruments typically include an angulated handle upper portion 40 relative to a handle lower portion 39. In this manner, the instrument structure of a multitude of instruments is accommodated by the configuration of the instant invention.

Figure 6:
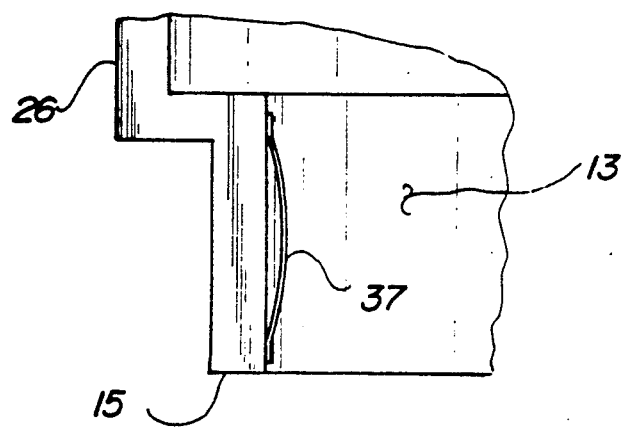
FIG. 6 is an orthographic view of section 6 as set forth in FIG. 5.
Figure 7:
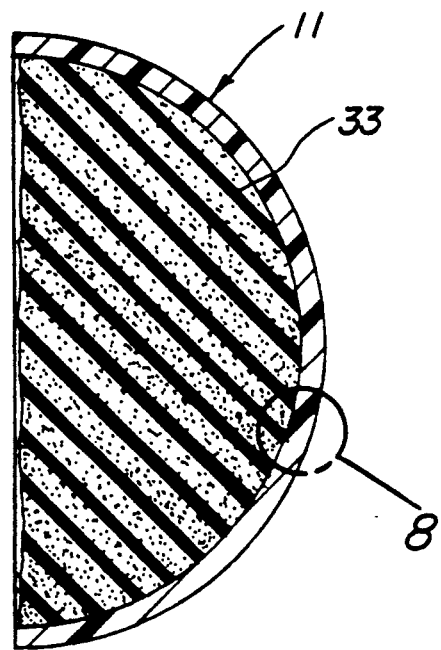
FIG. 7 is an orthographic view of section 7 as set forth in FIG. 5.
Figure 8:
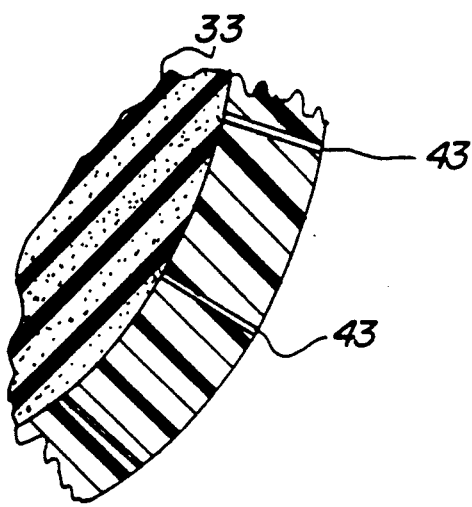
FIG. 8 is an orthographic enlarged view of section 8 as set forth in FIG. 7.

The FIG. 6 indicates the entrance openings 13 and 14, each including first and second leaf spring pairs 37 and 38 mounted within respective first and second entrance openings 13 and 14 at diametrically opposed sides thereof to secure the lower handle portion 39 relative to the structure. Each cover is further formed with first and second cover top walls 29 and 30 to completely encase an associated dental instrument. The first and second covers 11 and 12 accordingly define first and second cover cavities 31 and 32 that are coextensively filled with respective first and second polymeric foam inserts 33 and 34. To assist in venting relative to the instrument, and more specifically to the instrument head 41, vent bores 43 are directed through the second side wall first portions 24 in communication with the respective foam inserts 33 and 34 should an instrument be positioned within the foam inserts in a moistened condition, and it is understood that the foam inserts are of a fluid permeable material permitting subsequent venting to minimize bacteriological growth relative to the dental instrument.

Further it should be noted that respective first and second strap members 27 and 28 are mounted to the respective second and third portions of the second side wall. The first and second strap members are displaced relative to the first portion 24 of the second side wall of each of the covers 11 and 12 to minimize obstruction relative to access of the dental instrument. The straps are in turn securable to a fastener lug 42 mounted upon an opposing cover portion, as indicated in the FIG. 4 for example.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental instrument cover, comprising,
a first cover and a second cover, with the first cover and the second cover arranged in a coextensive mirror image configuration relative to one another, with the first cover having a first cavity, the second cover having a second cavity, and the first cavity and second cavity arranged in confronting cooperative relationship relative to one another in a first closed position, and the first cavity and the second cavity are spaced relative to one another in a second opened position when the first cover is spaced from the second cover, the first cover including a first cover first side wall and the second cover including a second cover first side wall, wherein the first cover first side wall and the second cover first side wall are of a longitudinally aligned configuration coextensive relative to one another, and the first cover including a first cover first end wall, the second cover including a second cover first end wall, the first cover first end wall including a first cover semi-cylindrical opening, the second cover first end wall including a second cover semi-cylindrical opening, wherein the first cover semi-cylindrical opening and the second cover semi-cylindrical opening define a cylindrical configuration in the first position,
and
the first cover having a first cover second end wall, and the second over having a second cover second end wall, wherein the first cover second end wall and the second cover second end wall are arranged orthogonally relative to the first cover first side wall and the second cover first side wall, and the first cover second end wall and the second cover second end wall are each of a second end wall length, wherein the first cover first end wall and the second cover first end wall are of a first end wall width less than the second end wall length, and including a first cover second side wall and a second cover second side wall, and the first cover second side wall and the second cover second side wall each include a first portion of arcuate configuration spaced relative to the first cover first side wall and the second cover first side wall a first spacing greater than the second end wall length, and the first cover and the second cover each including respective their portions parallel to the respective first cover first side wall and second cover first side wall, and the first cover second side wall and second cover second side wall each include a second side wall portion canted from the first portion to the second portion to accommodate an angulated handle of an associated dental instrument, and the first cavity and second cavity include respective first and second foam inserts coextensive therewith for securing a dental instrument when the first cover and second cover are in the first position, and the first insert and the second insert are each formed of a fluid permeable and porous polymeric foam material.

2. A dental instrument cover as set forth in claim 1 wherein the first entrance opening and the second entrance opening each include respective first leaf spring pair and second leaf spring pair, with the first leaf spring pair mounted in diametrically opposed orientation within the first entrance opening and the second leaf spring pair mounted in a diametrically opposed relationship through the second entrance opening to secure a dental instrument lower handle within the first entrance opening and the second entrance opening.

3. A dental instrument cover as set forth in claim 2 wherein at least one hinge member is mounted to the first cover first side wall and second cover first side wall to permit pivoting of the cover relative to the second cover.

4. A dental instrument cover as set forth in claim 3 including at least one strap member mounted to the first cover cooperative with a strap fastener mounted to the second cover, with the strap member spaced from each first portion of the first cover second side wall and the second cover second side wall to permit ease of access to a dental instrument head.

5. A dental instrument cover as set forth in claim 4 wherein the first portion of the first cover second side wall includes a plurality of vent bores directed therethrough in communication with the first polymeric foam insert to permit venting of the first polymeric foam insert and the second polymeric foam insert when the first cover and the second cover are in the first position.

* * * * *